(12) United States Patent
McKinney

(10) Patent No.: US 6,660,262 B2
(45) Date of Patent: Dec. 9, 2003

(54) BROAD SPECTRUM ANTIMICROBIAL COMPOUND AND TREATMENT

(75) Inventor: Randy R. McKinney, Grangeville, ID (US)

(73) Assignee: Bovine Health Products, Inc., Grangeville, ID (US)

( * ) Notice: Subject to any disclaimer, the term of this patent is extended or adjusted under 35 U.S.C. 154(b) by 0 days.

(21) Appl. No.: 09/965,997

(22) Filed: Sep. 28, 2001

(65) Prior Publication Data

US 2003/0095950 A1 May 22, 2003

(51) Int. Cl.[7] .................... A61L 9/01; A01N 63/00; C12N 1/00; C12N 1/12; C12N 1/20
(52) U.S. Cl. .................. 424/93.4; 424/76.5; 424/76.6; 424/76.8; 424/439; 424/442; 424/813; 424/814; 424/815; 424/823; 424/824; 424/825; 424/829; 435/252.1; 435/822
(58) Field of Search .................... 424/93.1, 725, 424/76.5, 76.6, 76.8, 439, 442, 93.4, 813, 814, 815, 823, 824, 825, 829; 435/252.1, 822

(56) References Cited

U.S. PATENT DOCUMENTS

| 4,782,048 A | | 11/1988 | Upton |
|---|---|---|---|
| 5,496,567 A | | 3/1996 | McLean |
| 5,501,857 A | * | 3/1996 | Zimmer ....................... 424/438 |
| 5,976,579 A | | 11/1999 | McLean |
| 6,143,332 A | | 11/2000 | McLean |
| 6,197,763 B1 | | 3/2001 | Hepworth Thompson et al. |
| 6,242,009 B1 | | 6/2001 | Batarseh et al. |
| 6,365,152 B1 | * | 4/2002 | McKinney ................. 424/93.4 |
| 6,399,114 B2 | * | 6/2002 | Foreman |

* cited by examiner

*Primary Examiner*—Leon B. Lankford, Jr.
*Assistant Examiner*—Deborah K. Ware
(74) *Attorney, Agent, or Firm*—Richard D. Clarke

(57) ABSTRACT

A new and improved formulation and method for making same, for a broad spectrum antimicrobial treatment for bacterial and viral infections in cattle, horses, pigs, sheep and other domestic and non-domestic animals. More particularly, the present invention relates to a treatment which enables rapid relief of symptoms in an affected animal with a mortality of less than 1 percent by providing trace organic minerals in microgram quantities which act as nutrients for the animal. The treatment provides further nutritional requirements in the form of vitamin A, folic acid and vitamin $D_3$ supplements, cobalt amino acid chelates and dried kelp, a source of minerals, amino acids, simple and complex carbohydrates, iodine and fiber. In addition, a bacterial innoculum consisting of Acidophilus species is introduced which would inhibit growth of pathogenic or opportunistic species of bacteria by competition for nutrients as well as providing for required vitamins as a by-product of metabolism.

22 Claims, No Drawings

BROAD SPECTRUM ANTIMICROBIAL COMPOUND AND TREATMENT

BACKGROUND OF THE INVENTION

1. Field of the Invention

The present invention relates to a new and improved broad spectrum antimicrobial compound for use in treatment of bacterial and viral infections in cattle, horses, pigs, sheep, goats, dogs, cats and other domestic and non-domestic animals and the method of making and using it. More particularly, the present invention relates to a composition formulated from two groups of compounds, when combined and properly administered to infected animals suffering from a broad spectrum of pathogens including fungal, viral or bacterial infections, acts to rapidly relieve the symptoms associated with those infections and diseases. The compounds utilized in the two groups radically depart from conventional treatments.

2. Description of the Related Art

Cattle, pigs, sheep and other domestic animals are a widely used source of protein and wealth in a major portion of the world today. With a number of third world countries struggling to feed a growing number of impoverished people, affordable, efficient treatments for common diseases of domestic as well as non-domestic animals are becoming increasingly important.

One such disease affecting domesticated animals which is of great concern is foot and mouth disease (FMD). FMD is considered to be the most economically devastating livestock disease in the world. Although the United States as well as Central America, Australia, New Zealand and Chile as well as some countries in Europe are considered free of, local, state and federal agencies are on heightened alert against outbreaks of the disease. There have been reports of various types of foot and mouth disease virus in Africa, South America, Asia and part of Europe. The U.S. Department of Agriculture has prohibited the importation of live swine and ruminants and any fresh swine or ruminant meat or products from Great Britain or Northern Ireland and is retroactive to January 2001. In addition, enhanced surveillance of travelers coming from Europe is being enforced. This has potentially devastating ramifications for the economies of those countries as well as presenting a high cost for other countries in terms for surveillance and enforcement of import restrictions.

Foot and mouth disease is a highly contagious and economically devastating disease which may infect cattle, swine, sheep, goats, deer and other cloven-hoofed ruminants. Many affected animals recover, but the disease leaves them debilitated. The disease may cause losses in production of meat and milk and because it spreads rapidly, it is one of the diseases that livestock owners dread most. An outbreak could cost billions of dollars in losses in the first year. The most serious effects of the disease in dairy cattle are loss of milk and yield.

The disease is caused by a virus which can be spread by animals, people, or materials that bring the virus into physical contact with susceptible animals. There are seven different types and more than 60 subtypes of FMD virus, and there is no universal vaccine against the disease. Animals that receive the vaccine usually develop some degree of protection against clinical signs of FMD within 7 to 8 days. Any wide-scale vaccination program would be extremely costly to undertake and would have minimal effects against any strains that were not included in the vaccination series.

The longstanding response to foot and mouth disease includes eradicating the disease by depopulating affected and exposed animals. After confirmation of an outbreak, infected or exposed animals would be quarantined and destroyed.

Foot and mouth disease is only one of a long list of diseases which affect domesticated and wild animals in the United States as well as the world. FMD can also be confused with several similar but less harmful diseases such as vesicular stomatitis, bluetongue, bovine viral diarrhea, and foot rot in cattle, vesicular exanthema of swine, and swine vesicular disease.

Other foreign diseases of concern to livestock producers include African swine fever, African horse sickness, bovine spongiform encephalopathy, classical swine fever, contagious bovine pleuropneumonia, exotic Newcastle disease, Rift Valley fever, rinderpest and swine vesicular disease, among others. In addition, there are numerous domestic diseases that represent suffering for domestic animals as well as economic hardships for owners. In addition, several diseases threaten the fragile existence of endangered species as well. These diseases cause untold hardships on third world countries including contributing to the suffering of inhabitants of already drought and disaster stricken areas of the world least able to afford expensive antibiotic treatments.

As previously discussed, vaccination against most bacterial, viral and fungal infections affecting domestic and non-domestic animals is usually not employed because the cost of vaccination programs is prohibitive. Because of the number of serotypes of pathogenic species, vaccination may not be an effective preventative measure against even one disease causing agent.

Another factor in the treatment of bacterial, viral and fungal infections affecting domesticated and non-domesticated animals is the rise in antibiotic resistant strains. These antibiotic resistant strains of bacteria and other infectious agents are becoming an increasing threat to livestock and are posing a threat to other species as well. In addition, infection by multiple agents causing similar symptoms might render such treatments ineffective. Results from diagnostic laboratories have indicated that several etiologic agents can be simultaneously associated with one afflicted animal. This type of multiple etiology may make any antibiotic treatment ineffective.

The benefits of antimicrobial compounds designed for ameliorating the symptoms of the disease are well known. Examples of different types and kinds of compositions and techniques for treatment of symptoms of various diseases are disclosed in U.S. Pat. Nos. 6,197,763 and 4,782,048.

Antimicrobial treatments for symptoms of viral, bacterial and fungal diseases are known in the prior art. Such a treatment is described in U.S. Pat. No. 6,197,763. This inventive formulation includes dietary metals, selected from zinc, copper, cobalt, manganese and iron and a dietary ligand, either lawsone or topolone. The formulation specifically treats gastrointestinal symptoms and gastrointestinal microbes.

This novel invention was used in conjunction with standard antibiotic therapy which included amoxicillin in clinical trials. While in vitro tests against Helicobacter pylori indicated antimicrobial activity, it is unclear from field studies as to the effectiveness of the novel compound without the addition of the standard antibiotic treatment. It is also unclear as to the length of time from the beginning of treatment to the relief of symptoms from the information provided.

The presence of the amoxicillin also means that normal intestinal flora is probably destroyed as well as the infecting organism. The normal intestinal flora are crucial for proper nutrition for the animal during a period of time when the body is being particularly stressed.

Additionally, tropolone is known to be an amino glycoside inactivating enzyme. Lawsone is an RNA/DNA antimetabolite. Both of these compounds are known to have antibiotic properties. While these compounds may be found in extracts of naturally occurring products, the purified compounds themselves are relatively expensive.

Therefore, it would be highly desirable to have a new and improved broad spectrum antimicrobial compound for use in treatment of bacterial, fungal and viral infections in cattle, horses, pigs, sheep and other domestic and non-domestic animals which would allow rapid relief from the symptoms, which would not depend upon standard antibiotic treatment and which would introduce beneficial micro-organisms to recolonize the intestinal tract in order to provide for needed vitamin and nutritional needs of the animal and provide a bacterial population that would effectively compete with pathogenic organisms which may still be present.

In addition, it would be highly desirable to have such a novel broad spectrum antimicrobial composition which would be comprised of relatively inexpensive and readily available ingredients, easily stored and transported. Such a composition would also be economical to manufacture.

The treatment described in U.S. Pat. No. 4,782,048 addresses the problem of providing for a formulation which would be economical to manufacture. However, the recommendations for usage address only one particular illness and the application is topical. The topical application limits the time period that the infecting organism is in direct contact with the antimicrobial compound.

In addition, there is no information provided as to the efficacy of the compound in vivo or the required length of treatment before symptoms of the disease are relieved.

Therefore, it would be highly desirable to have a new and improved formulation and method for using same for broad spectrum antimicrobial compound for use in treatment of bacterial and viral infections in cattle, horses, pigs, sheep and other domestic and non-domestic animals which would allow rapid relief from the symptoms of a variety of diseases and be proven to be efficacious in vivo.

SUMMARY OF THE INVENTION

Therefore, the principal object of the present invention is to provide a new and improved formulation and method of using same, for a broad spectrum antimicrobial compound and treatment for bacterial and viral infections in cattle, horses, pigs, sheep and other domestic and non-domestic animals.

It is a further object of the present invention to provide such a new and improved formulation and method for using same, for a broad spectrum antimicrobial compound and treatment for bacterial, fungal and viral infections in cattle, horses, pigs, sheep and other domestic and non-domestic animals the relieves symptoms within a very short period of time with little or no toxicity for the animal being treated.

It is a further object of the present invention to provide such a new and improved formulation and method for using same, for a broad spectrum treatment for bacterial, fungal and viral infections in animals, which would introduce beneficial bacterial populations to recolonize the gastrointestinal tract of affected animals. The beneficial bacteria introduced would compete with pathogenic or opportunistic bacteria and would provide necessary nutrients as by-products to the affected animals.

It is yet a further object of the present invention to provide such a new and improved formulation and method for using same, for broad spectrum antimicrobial treatment for bacterial, fungal and viral infections in animals, that would be easy to ship and store and which provides relief from symptoms to the affected animal very rapidly upon application. The formulation of the treatment provides a simple, yet effective means by which to treat infected animals.

It is a further object of the present invention to provide such a new and improved formulation and method for using same, for a broad spectrum antimicrobial compound and treatment for bacterial, fungal and viral infections in animals that is inexpensive to produce.

It is a further object of the present invention to provide such a new and improved formulation and method for using same, for a broad spectrum antimicrobial compound and treatment for bacterial, fungal and viral infections in cattle, horses, pigs, sheep and other domestic and non-domestic animals formulated with essential minerals and naturally occurring ingredients that would not select for strains of pathogens with a resistance to antibiotics.

Briefly, the above and further objects of the present invention are realized by providing a new and improved formulation and method for using same, for a broad spectrum antimicrobial treatment for bacterial and viral infections in cattle, horses, pigs, sheep, goats, dogs, cats and other domestic and non-domestic animals. More particularly, the present invention relates to a treatment which enables rapid relief of symptoms in an affected animal with little or no toxicity exhibited for the host animal. The treatment provides further nutritional requirements in the form of vitamin A, folic acid and vitamin $D_3$ supplements, cobalt amino acid chelates and dried kelp, a source of minerals, amino acids, simple and complex carbohydrates, iodine and fiber. In addition, a bacterial inoculum consisting of Acidophilus species is introduced which would inhibit growth of pathogenic or opportunistic species of bacteria by competition for nutrients as well as providing for required vitamins as a by-product of metabolism.

DESCRIPTION OF THE PREFERRED EMBODIMENT

The treatment for bacterial and viral infections in cattle, horses, pigs, sheep and other domestic and non-domestic animals of the present invention is comprised in a liquid state of trace minerals, cobalt amino acid chelates, Acidophilus sp., kelp and vitamins in a solution using distilled water as the carrier.

Trace mineral elements have been linked to immune system health, cell growth enhancement, glucose tolerance factor and other overall health concerns. Furthermore, metal ions have been shown to have certain antimicrobial properties. The above mentioned trace elements, when combined in the current formulation have an unexpected synergy in treatment of a diseased animal.

The second solution used to formulate the new treatment composition is composed of a bacterial species that would recolonize the gastrointestinal tract as well as a nutritional formulation to provide needed vitamins and minerals to the affected animal. In addition, kelp, a natural source of carbohydrates, amino acids, vitamins, minerals and trace elements is also added. Kelp contains over 60 minerals and elements including iodine, 21 amino acids, simple and complex carbohydrates. It is believed to be a promoter of glandular health, especially for the pituitary, adrenal and thyroid glands. The thyroid and pituitary glands regulate certain functions of digestion. Kelp also provides a natural source of fiber.

After the two solutions are mixed, an oral dose of approximately 10–15 ml. of the resultant treatment solution is administered to the affected animal. The dose is repeated every 24 hours until symptoms are relieved. After the animal responds to the treatment, and regains its appetite, a regular diet and feeding schedule can be resumed. Furthermore, with the instant treatment for bacterial, fungal and viral infections in cattle, horses, pigs, sheep and other domestic and non-domestic animals composition, there is no requirement for isolation and identification of the causative agent or antimicrobial sensitivity testing of etiologic agents in order to determine antibiotic resistance.

In addition, because the present composition does not incorporate synthetic antibiotics such as penicillin or amoxycillin, there is no selection for antibiotic resistant strains of bacteria which would necessitate concurrent or sequential administration of antibiotics.

The present composition was administered on the above-noted 24 hour cycle to several test groups of infected animals. There was no mortality among those animals treated with the present treatment for bacterial and viral infections. Affected animals that were treated with the present composition were asymptomatic after 1 to six days of treatments.

EXAMPLE 1

A field trial was conducted where 15 yearling calves, all diagnosed with pneumonia, were each treated with 10 milliliters of the present treatment for bacterial and viral infections. The dose was administered orally once a day for up to 5 days. Of these treated calves, 33% were asymptomatic within 24 hours after having been given only one dose of the present composition. Eight calves were asymptomatic within 48 hours having been given 2 doses. The other two calves were asymptomatic after 4 dosages.

EXAMPLE 2

A second field trial included one Limousin bull diagnosed with pneumonia. The normal weight of the bull was 1,950 pounds but at the time of treatment, the weight was 1,625 pounds. The bull had experienced a weight loss of 325 pounds since the onset of symptoms. The bull would not eat or drink, had a severe dry cough with no discharge from the nose, was weak and lethargic.

The bull was administered an oral dosage of 30 milliliters of the present composition. Within one hour, he was eating hay and drinking water. He was asymptomatic within 3 days. On the seventh day, still asymptomatic, he was given a 30 milliliter follow up dose. The bull fully recovered and regained his normal weight. He was being used in a registered Limousin breeding program.

EXAMPLE 3

A third field trial was conducted on two Hereford crossbred calves. The 4 month old calves were diagnosed with coccsidiosis. The symptoms included profuse, watery green stool with mucous and large amounts of bright red blood. Both calves were weak. One calf, #178, had these symptoms for seven days without treatment and was steadily getting worse. The other calf, #162, had been sick for 3 days.

Both calves were given oral doses of 15 milliliters of the novel treatment for bacterial and viral infections once a day for two days. After the first administration, both calves were in a much improved condition. Both were asymptomatic within 48 hours after having received a total of two doses of the present composition.

EXAMPLE 4

A fourth field trial was conducted on 23 horses in a herd of 165. The horses showing symptoms had deep rumbling cough, profuse green/yellow mucous discharge from both nostrils, dull glassy eyes, lowered heads, and were lethargic and despondent. The infected horses had displayed these symptoms for 7 to 20 days. Symptoms continued to worsen with continued duration of the disease.

All 23 horses were given 15 milliliters of the current composition once a day. Nine of these horses were asymptomatic after 48 hours and two doses. Ten horses were asymptomatic within four days having been administered three doses. Four horses were asymptomatic within six days having been given five doses.

EXAMPLE 5

A fifth field trial was conducted on a Hereford crossbred cow. The cow had been diagnosed with foot rot in her left hind foot. She could not put any weight on it. The foot was swollen twice the normal size and red in color between the toes and around the comet band. There was a hole in the sole of the left toe at the heel, ½ inch in diameter, which was oozing putrefied matter.

The cow was given an oral dose of 30 milliliters of the present composition. In addition, the novel treatment compound was administered topically around the cornet band and 10 milliliters was injected into the hole in the sole of the left toe using a needle-less syringe.

Within four days, the cow was walking on that foot. At that time, the oral and topical administration was repeated using the same protocol. Within seven days of the second administration, the cow was fully recovered.

These field tests demonstrated that the current composition for treatment infections in animals worked on a broad range of pathogens with no recurrence of symptomology. All animals recovered in a very short period of time with bright eyes, shiny coats, good appetites and vigorous carriage.

In addition to the field trials conducted with the present composition for treatment of disease in animals, minimum inhibitory concentrations of the composition were determined for several bacteria and one mycotic organism. The protocol for performing this test is found in the National Committee for Clinical Laboratory Standards 9NCCLS) publication M7-T2. The tests were conducted by Larry W. Harris, Registered Microbiologist RM (N.R.M.) 3053.

The minimum inhibitory concentration (MIC) measures the ability of the antimicrobial agent to inhibit multiplication of the organisms being challenged. Thus, organisms in the innoculum are inhibited from replicating by the antimicrobial agent. Examples of bacteriostatic agents are chloramphenicol and erythromycin, nalidixic acid, sulfonamides and tetracyclines.

Dilutions of the present composition were made in a nutrient broth. The nutrient broth is known to support growth of the organisms used to challenge the efficacy of the composition. A one to ten, a one to one hundred dilution and a one to one thousand dilution of the present composition were made in the nutrient broth.

Further dilutions of each concentration were made as follows in Table 1 below:

TABLE 1

| TUBE NUMBER | AMOUNT OF TEST SOLUTION (milliliters) | AMOUNT OF NUTRIENT BROTH (milliliters) | TOTAL AMOUNT IN EACH TUBE (milliliters) |
|---|---|---|---|
| 1 | 1.0 | 0.0 | 1.0 |
| 2 | 0.9 | 0.1 | 1.0 |
| 3 | 0.8 | 0.2 | 1.0 |
| 4 | 0.7 | 0.3 | 1.0 |
| 5 | 0.6 | 0.4 | 1.0 |
| 6 | 0.5 | 0.5 | 1.0 |
| 7 | 0.4 | 0.6 | 1.0 |
| 8 | 0.3 | 0.7 | 1.0 |
| 9 | 0.2 | 0.8 | 1.0 |
| 10 | 0.1 | 0.9 | 1.0 |
| Control | 0.0 | 1.0 | 1.0 |

The undiluted antimicrobial composition and 1:10, 1:100 and 1:1000 dilutions were each diluted as indicated in the chart above resulting in a set of 11 tubes for each. All of the tubes then received, one milliliter (ml) of nutrient broth. At this point each tube contained 2 ml.

A bacterial suspension was added to each tube. 0.1 ml of the test organism suspension $1 \times 10^6$ CFU/ml, where CFU is an abbreviation for colony forming units, was added to each tube.

Each tube contained 2.1 milliliters of liquid at this point with a concentration of $2.5 \times 10^4$ CFU/ml. of the challenge innoculum. This procedure was conducted using four bacteria as the challenge innoculum. Two gram negative organisms, *Psuedomonas aeruginosa* and K-12 *Escherichia coli* were used as challenge organisms. Two gram positive organisms, *Staphyloccocus aureus,* and *Bacillus subtilis* were used as challenge organisms.

The tubes were then incubated at 35° C. over night. The tubes that were turbid were evaluated to have growth of bacteria. The nonturbid tubes were determined to be negative for growth of bacteria (see Table 2 below).

TABLE 2

Nutrient Broth
OVERNIGHT TEST TUBE INCUBATION AT 35 C.

| Tube | 1 | 2 | 3 | 4 | 5 | 6 | 7 | 8 | 9 | 10 |
|---|---|---|---|---|---|---|---|---|---|---|
| undiluted | − | − | − | − | − | − | − | − | − | − |
| 1/10 dilution | − | − | − | − | − | − | − | − | − | − |
| 1/100 dilution | − | − | − | − | − | − | + | + | + | + |
| 1/1000 dilution | + | + | + | + | + | + | + | + | + | + |

+ = Turbid (growth)
− = Nonturbid (no growth)

After overnight incubation of the tubes, 0.001 ml from the control tube and each of the non-turbid tubes was subcultured to nutrient agar, mannitol-salt agar and MacConkey agar (see Table 3, Table 4 and Table 5 below). These subcultures were incubated at 35° C. overnight. CFU on subcultures were determined. Additionally, 0.001 ml of the broth from control tubes were subcultured to agar resulting in a count of 250 colonies.

TABLE 3

Nutrient Agar
(supports both gram negative and gram positive bacterial growth)
OVERNIGHT PLATE INCUBATION AT 35 C.

| Plate | 1 | 2 | 3 | 4 | 5 | 6 | 7 | 8 | 9 | 10 |
|---|---|---|---|---|---|---|---|---|---|---|
| undiluted | − | − | − | − | − | − | − | − | − | − |
| 1/10 dilution | − | − | − | − | − | − | − | − | − | − |
| 1/100 dilution | − | − | + | + | + | + | + | + | + | + |
| 1/1000 dilution | + | + | + | + | + | + | + | + | + | + |

+ = growth
− = no growth

The MIC for all organisms was established at 0.409% concentration of the present antimicrobial composition.

TABLE 4

Mannitol-Salt Agar (supports gram positive bacterial growth)
OVERNIGHT PLATE INCUBATION AT 35 C.

| Plate | 1 | 2 | 3 | 4 | 5 | 6 | 7 | 8 | 9 | 10 |
|---|---|---|---|---|---|---|---|---|---|---|
| undiluted | − | − | − | − | − | − | − | − | − | − |
| 1/10 dilution | − | − | − | − | − | − | − | − | − | − |
| 1/100 dilution | − | − | − | − | − | − | − | − | − | − |
| 1/1000 dilution | − | − | − | − | − | − | − | + | + | + |

+ = growth
− = no growth

The MIC for gram positive organisms was established at 0.018% concentration of the current composition.

TABLE 5

MacConkey Agar (supports gram negative bacterial growth)
OVERNIGHT PLATE INCUBATION AT 35 C.

| Plate | 1 | 2 | 3 | 4 | 5 | 6 | 7 | 8 | 9 | 10 |
|---|---|---|---|---|---|---|---|---|---|---|
| undiluted | − | − | − | − | − | − | − | − | − | − |
| 1/10 dilution | − | − | − | − | − | − | − | − | − | − |
| 1/100 dilution | − | − | + | + | + | + | + | + | + | + |
| 1/1000 dilution | + | + | + | + | + | + | + | + | + | + |

+ = growth
− = no growth

The MIC for gram negative organisms was established at 0.409% concentration of the present antimicrobial composition.

In addition, efficacy of the present composition against mycotic organisms was tested. The Minimum Inhibitory Concentration (MIC) of the present composition was established using the previously described protocol. Again, the Minimum Inhibitory Concentration is that concentration of the compound which successfully prevents multiplication of the organisms being challenged.

A one to ten, a one to one hundred dilution and a one to one thousand dilution of the present composition were made in the Sabouraud Dextrose broth. Sabouraud Dextrose broth is known to support growth of mycotic organisms used to challenge the efficacy of the composition. The results are illustrated in Table 7 below.

Further dilutions of each concentration were made as follows in Table 6 below:

TABLE 6

| TUBE NUMBER | AMOUNT OF TEST SOLUTION (milliliters) | AMOUNT OF NUTRIENT BROTH (milliliters) | TOTAL AMOUNT IN EACH TUBE (milliliters) |
|---|---|---|---|
| 1 | 1.0 | 0.0 | 1.0 |
| 2 | 0.9 | 0.1 | 1.0 |
| 3 | 0.8 | 0.2 | 1.0 |
| 4 | 0.7 | 0.3 | 1.0 |
| 5 | 0.6 | 0.4 | 1.0 |
| 6 | 0.5 | 0.5 | 1.0 |
| 7 | 0.4 | 0.6 | 1.0 |
| 8 | 0.3 | 0.7 | 1.0 |
| 9 | 0.2 | 0.8 | 1.0 |
| 10 | 0.1 | 0.9 | 1.0 |
| Control | 0.0 | 1.0 | 1.0 |

The undiluted antimicrobial composition and 1:10, 1:100 and 1:1000 dilutions were each diluted as indicated in the chart above resulting in a set of 11 tubes for each. All of the tubes then received, one milliliter (ml) of nutrient broth. At this point each tube contained 2 ml.

A suspension of the test organism was added to each tube. 0.1 ml of the test organism suspension $1 \times 10^6$ CFU/ml, where CFU is an abbreviation for colony forming units, was added to each tube.

Each tube contained 2.1 milliliters of liquid at this point with a concentration of $2.5 \times 10^4$ CFU/ml. of the challenge innoculum, in this case, *Saccharomyces cerevisiae*.

The tubes were then incubated at 35° C. over night. The tubes that were turbid were evaluated to have growth of the organism. The nonturbid tubes were determined to be negative for growth of the organism.

TABLE 7

Sabouraud Dextrose Broth
OVERNIGHT TEST TUBE INCUBATION AT 35 C.

| Tube | 1 | 2 | 3 | 4 | 5 | 6 | 7 | 8 | 9 | 10 |
|---|---|---|---|---|---|---|---|---|---|---|
| undiluted | – | – | – | – | – | – | – | – | – | – |
| 1/10 dilution | – | – | – | – | – | – | – | – | – | – |
| 1/100 dilution | – | – | – | – | – | – | + | + | + | + |
| 1/1000 dilution | + | + | + | + | + | + | + | + | + | + |

+ = Turbid (growth)
– = Nonturbid (no growth)

After overnight incubation of the tubes, 0.001 ml from the control tube and each of the non-turbid tubes was subcultured to Sabouraud Dextrose agar. These subcultures were incubated at 35° C. overnight. CFU on subcultures were determined. Additionally, 0.001 ml of the broth from control tubes were subcultured to agar resulting in a count of 250 colonies. The results are illustrated in Table 8 below.

TABLE 8

Sabouraud Dextrose Agar (supports mycotic organism growth)
OVERNIGHT PLATE INCUBATION AT 35 C.

| Plate | 1 | 2 | 3 | 4 | 5 | 6 | 7 | 8 | 9 | 10 |
|---|---|---|---|---|---|---|---|---|---|---|
| undiluted | – | – | – | – | – | – | – | – | – | – |
| 1/10 dilution | – | – | – | – | – | – | – | – | – | – |
| 1/100 dilution | – | – | – | – | – | – | – | – | – | – |
| 1/1000 dilution | – | – | – | – | – | – | – | + | + | + |

+ = growth
– = no growth

The MIC for mycotic organisms was established at 0.018% concentration of the present antimicrobial composition.

The treatment for bacterial and viral infections in cattle, horses, pigs, sheep and other domestic and non-domestic animals of the present invention is comprised in a liquid state of 22 constituents. These constituents are formulated in two liquid solutions (a group 1 and group 2 solution) which are then combined and stored in liquid form. The composition is readily available in this form for administration to the animal at 10–15 ml per dose most commonly at 24 hour intervals.

The first solution (the group 1 solution) is composed of trace minerals in microgram amounts. The following is a list of trace minerals with the approximate amount of each in micrograms (mcg) and showing the relative percentage of each trace mineral elements when suspended in solution:

| | | |
|---|---|---|
| Cobalt | 200 mcg | 19% |
| Copper | 200 mcg | 19% |
| Silicon | 120 mcg | 11.5% |
| Neodymium | 100 mcg | 9.5% |
| Praseodymium | 100 mcg | 9.5% |
| Nickel | 70 mcg | 6.7% |
| Chlorine | 65 mcg | 6.2% |
| Zinc | 62 mcg | 5.9% |
| Yttrium | 60 mcg | 5.7% |
| Strontium | 15 mcg | 1.4% |
| Titanium | 15 mcg | 1.4% |
| Aluminum | 15 mcg | 1.4% |
| Chromium | 10 mcg | 0.95% |
| Gallium | 10 mcg | 0.95% |
| Rubidium | 10 mcg | 0.95% |
| Total trace minerals | 1052 mcg | 100% |

The trace organic minerals are suspended in a liquid carrier prior to final formulation of the new treatment composition. Said liquid carrier is typically distilled water.

The following are the constituents of the second solution (the group 2 solution) suspended in 1 oz. of distilled water:

| | |
|---|---|
| Acidophulus sp. | 3.0 grams |
| Dried kelp | 1.0 gram |
| Folic acid | 1.0 gram |
| Vitamin A supplement | 0.5 grams |
| Vitamin $D_3$ supplement | 0.5 grams |
| Cobalt amino acid chelates | 0.2 grams |

All ingredients are mechanically mixed to form the liquid composition which may then be administered orally to affected animals in doses of 10 to 15 ml. When mixed, the final ratio of group 1 solution to group 2 solution is 24 parts group 1 solution to 1 part group 2 solution, or 24:1 respectively.

A needle-less syringe is used to administer the required dosage into the back of the affected animals mouth. This treatment is repeated every 24 hours as needed. In severe cases, the dosage can be increased to 15 to 30 ml every 24 hours until the afflicted animal is asymptomatic.

It should be understood, however, that even though these numerous characteristics and advantages of the invention have been set forth in the foregoing description, together with details of the composition and method of application of the invention, the disclosure is illustrative only, and changes may be made in detail, especially in matters of chemistry, dosage and implementation within the principal of the invention to the full extent indicated by the broad general meaning of the terms in which the appended claims are expressed.

What is claimed is:

1. A broad spectrum antimicrobial compound for use in animals comprising:
   (a) a trace minerals solution containing organic mineral elements;
   (b) an Acidophilus sp. innoculum;
   (c) a vitamin solution containing vitamin A, vitamin D, and folic acid;
   (d) cobalt amino acid chelates; and
   (e) dried kelp, whereby said Acidophilus sp. innoculum, vitamin solution, cobalt amino acid chelates and dried kelp are mixed together in distilled water prior to mixing with said trace minerals solution; and
   said trace minerals solution is mixed with said Acidophilus sp. innoculum, vitamin solution, cobalt amino acid chelates and dried kelp solution in the ratio of 24:1 to complete the formulation of said broad spectrum antimicrobial compound.

2. The broad spectrum antimicrobial compound for use in animals according to claim 1, wherein said trace minerals solution containing organic mineral elements includes about 19% cobalt, about 19% copper, about 11.5% silicon, about 9.5% neodymium, and about 9.5% praseodymium.

3. The broad spectrum antimicrobial compound for use in animals according to claim 2, wherein said trace minerals solution containing organic mineral elements further includes about 6.7% nickel, about 6.2% chorine, about 5.9% zinc and about 5.7% yttrium.

4. The broad spectrum antimicrobial compound for use in animals according to claim 3, wherein said trace minerals solution containing organic mineral elements further includes about 1.4% strontium, about 1.4% titanium, and about 1.4% aluminum.

5. The broad spectrum antimicrobial compound for use in animals according to claim 4, wherein said trace minerals solution containing organic mineral elements further includes about 0.95% chromium, about 0.95% gallium and about 0.95% rubidium.

6. The broad spectrum antimicrobial compound for use in animals according to claim 1, wherein said Acidophilus sp. innoculum is added to the combination Acidophilus sp. innoculum, vitamin solution, cobalt amino acid chelates and dried kelp solution, by mixing about 3 grams of Acidophilus sp. innoculum per about one ounce of distilled water containing said vitamin solution, cobalt amino acid chelates and dried kelp solution.

7. The broad spectrum antimicrobial compound for use in animals according to claim 1, wherein said vitamin solution containing vitamin A, vitamin D, and folic acid includes about 1 gram of folic acid, about 0.5 grams of vitamin A, and about 0.5 grams of vitamin D added to about one ounce of distilled water.

8. The broad spectrum antimicrobial compound for use in animals according to claim 1, wherein said cobalt amino acid chelates is added to the combination Acidophilus sp. innoculum, vitamin solution, cobalt amino acid chelates and dried kelp solution, by mixing about 0.2 grams of cobalt amino acid chelates per about one ounce of distilled water containing said Acidophilus sp. innoculum, vitamin solution, and dried kelp solution.

9. The broad spectrum antimicrobial compound for use in animals according to claim 1, wherein said dried kelp is added to the combination Acidophilus sp. innoculum, vitamin solution, cobalt amino acid chelates and dried kelp solution, by mixing about one gram of dried kelp to about one ounce of distilled water containing said Acidophilus sp. innoculum, vitamin solution, and cobalt amino acid chelates.

10. A method for treating animals afflicted with a microbial infection using the broad spectrum antimicrobial compound according to claim 1, comprising the step of:
    (a) administering the broad spectrum antimicrobial compound in oral doses of about 10 to about 15 milliliters per animal per 24 hour period until the animal is asymptomatic.

11. The method of treating animal afflicted with a microbial infection according to claim 10, wherein said step of administering said broad spectrum antimicrobial compound includes adding said broad spectrum antimicrobial compound as an additive to the afflicted animals feed.

12. A method for treating animals afflicted with a microbial infection using the broad spectrum antimicrobial compound according to claim 1, comprising the step of:
    (a) administering said broad spectrum antimicrobial compound and treatment compound includes administering about 15 to about 30 milliliters per animal per 24 hour period for three days in severe cases of acute diarrhea and dehydration.

13. The method of treating animal afflicted with a microbial infection according to claim 12, wherein said step of administering said broad spectrum antimicrobial compound includes adding said broad spectrum antimicrobial compound as an additive to the afflicted animals feed.

14. A method of making a broad spectrum antimicrobial compound for use in animals, comprising the steps:
    (a) providing a trace minerals solution containing organic mineral elements;
    (b) providing an Acidophilus innoculum;
    (c) providing a vitamin solution containing vitamin A, vitamin D, and folic acid;
    (d) providing cobalt amino acid chelates; and
    (e) providing dried kelp, whereby said Acidophilus innoculum, vitamin solution, cobalt amino acid chelates and dried kelp are mixed together in distilled water prior to mixing with said trace minerals solution; and
    (f) mixing said trace minerals solution added in 24 parts with, and said Acidophilus sp. innoculum, vitamin solution, cobalt amino acid chelates and dried kelp added in one part, to complete the formulation of said broad spectrum antimicrobial compound.

15. The method of making a broad spectrum antimicrobial compound according to claim 14, wherein said step of providing a trace minerals solution containing organic mineral elements further includes the step of providing a trace minerals solution containing about 19% cobalt, about 19% copper, about 11.5% silicon, about 9.5% neodymium, and about 9.5% praseodymium.

16. The method of making a broad spectrum antimicrobial compound according to claim 15, wherein said step of providing a trace minerals solution containing organic mineral elements further includes the step of providing a trace minerals solution containing about 6.7% nickel, about 6.2% chorine, about 5.9% zinc and about 5.7% yttrium.

17. The method of making a broad spectrum antimicrobial compound according to claim 16, wherein said step of providing a trace minerals solution containing organic mineral elements further includes the step of providing a trace minerals solution containing about 1.4% strontium, about 1.4% titanium, and about 1.4% aluminum.

18. The method of making a broad spectrum antimicrobial compound according to claim 17, wherein said step of providing a trace minerals solution containing organic mineral elements further includes the step of providing a trace minerals solution containing about 0.95% chromium, about 0.95% gallium and about 0.95% rubidium.

19. The method of making a broad spectrum antimicrobial compound according to claim 17, wherein said step of providing an Acidophilus innoculum, includes the step of providing an Acidophilus innoculum in the concentration of about 3 grams in about one ounce of distilled water.

20. The method of making a broad spectrum antimicrobial compound according to claim 17, wherein said step of providing a vitamin solution containing vitamin A, vitamin D, and folic acid, includes the step of providing a vitamin solution containing vitamin A, vitamin D, and folic acid in a concentration of about one gram folic acid, about 0.5 grams vitamin A, and about 0.5 grams vitamin D in about one ounce of distilled water.

21. The method of making a broad spectrum antimicrobial compound according to claim 17, wherein said step of providing cobalt amino acid chelates, includes the step of providing cobalt amino acid chelates in the concentration of about 0.2 grams in about one ounce of distilled water.

22. The method of making a broad spectrum antimicrobial compound according to claim 17, wherein said step of providing dried kelp includes the step of providing dried kelp in the concentration fo about one gram of dried kelp in about one ounce of distilled water.

* * * * *